United States Patent
Sofranko et al.

(10) Patent No.: US 11,046,892 B1
(45) Date of Patent: Jun. 29, 2021

(54) OXIDATIVE CRACKING OF HYDROCARBONS

(71) Applicant: Bio2Electric, LLC, Woburn, MA (US)

(72) Inventors: John A. Sofranko, Weston, MA (US); Elena Y. Chung, Somerville, MA (US); William K. Wang, Woburn, MA (US); C. Andrew Jones, Newtown Square, PA (US)

(73) Assignee: EcoCatalytic Inc., Woburn, MA (US)

( * ) Notice: Subject to any disclaimer, the term of this patent is extended or adjusted under 35 U.S.C. 154(b) by 0 days.

(21) Appl. No.: 16/800,883

(22) Filed: Feb. 25, 2020

Related U.S. Application Data

(60) Provisional application No. 62/810,137, filed on Feb. 25, 2019, provisional application No. 62/810,272, filed on Feb. 25, 2019.

(51) Int. Cl.
*C10G 1/10* (2006.01)
*C07C 4/02* (2006.01)
(Continued)

(52) U.S. Cl.
CPC ............... *C10G 1/10* (2013.01); *C07C 4/025* (2013.01); *C07C 11/04* (2013.01); *C07C 11/06* (2013.01); *C07C 2529/40* (2013.01)

(58) Field of Classification Search
None
See application file for complete search history.

(56) References Cited

U.S. PATENT DOCUMENTS

| 2,493,038 A | 1/1950 | Snyder et al. |
| 3,651,121 A | 3/1972 | Duke et al. |
| (Continued) | | |

FOREIGN PATENT DOCUMENTS

| EP | 2576046 B1 | 11/2014 |
| EP | 2853521 A1 | 4/2015 |
| (Continued) | | |

OTHER PUBLICATIONS

Jordi Labs "Typical Molecular Weights of Common Polymers" pp. 1-5. Accessed May 21, 2020. (Year: 2020).*

(Continued)

*Primary Examiner* — Philip Y Louie
*Assistant Examiner* — Alyssa L Cepluch
(74) *Attorney, Agent, or Firm* — RatnerPrestia

(57) ABSTRACT

Aspects of the invention relate to producing olefins and other products by oxidative dehydrogenation cracking of a hydrocarbon feed. In one embodiment, the method includes oxidative cracking a hydrocarbon feed comprised of plastic waste. Methods of the present invention employ dual functional catalyst comprising solid acids and metal oxides, which are capable of selectively oxidizing hydrogen to water rather than combustion of the hydrocarbon feeds or products. Additional aspects of the invention demonstrate catalyst synthetic methods for encapsulating metal oxides in the internal channels and cages of solid acids, thereby improving the selective oxidation of hydrogen to water and decreasing feed and product oxidation. The re-oxidation of the thus reduced metal oxide transfer agents supplies heat to drive the endothermic cracking of the feed.

18 Claims, 5 Drawing Sheets

(51) Int. Cl.
    C07C 11/06    (2006.01)
    C07C 11/04    (2006.01)

(56) References Cited

U.S. PATENT DOCUMENTS

| | | | |
|---|---|---|---|
| 4,544,785 | A | 10/1985 | Withers et al. |
| 4,547,607 | A | 10/1985 | Jones et al. |
| 4,599,477 | A | 7/1986 | Robinson et al. |
| 4,670,619 | A | 6/1987 | Withers, Jr. et al. |
| 4,777,313 | A | 10/1988 | Sofranko et al. |
| 4,830,728 | A | 5/1989 | Herbst et al. |
| 5,026,947 | A | 6/1991 | Mazurek |
| 5,079,385 | A | 1/1992 | Wu |
| 5,091,163 | A | 2/1992 | Gaffney et al. |
| 5,192,809 | A | 3/1993 | Jones et al. |
| 5,545,787 | A * | 8/1996 | Cooper ............... B01J 23/66 585/444 |
| 6,403,523 | B1 | 6/2002 | Cantrell et al. |
| 9,963,407 | B2 | 5/2018 | Stine et al. |
| 10,138,182 | B2 | 11/2018 | Sofranko et al. |
| 10,550,051 | B2 | 2/2020 | Li et al. |
| 2003/0181325 | A1* | 9/2003 | Ou ..................... B01J 23/34 502/302 |
| 2005/0124841 | A1* | 6/2005 | Rapier ................. C07C 5/48 585/658 |
| 2011/0245571 | A1 | 10/2011 | Kustov et al. |
| 2012/0041246 | A1 | 2/2012 | Scher et al. |
| 2012/0203042 | A1* | 8/2012 | Huber ................. C10B 57/06 585/241 |
| 2014/0275667 | A1* | 9/2014 | Sarker ................. C10G 1/10 585/241 |
| 2014/0371504 | A1 | 12/2014 | Stine et al. |
| 2016/0122264 | A1 | 5/2016 | Olbert et al. |
| 2017/0226030 | A1 | 8/2017 | Li et al. |
| 2019/0022626 | A1 | 1/2019 | Schammel et al. |
| 2019/0315667 | A1 | 10/2019 | Sofranko et al. |
| 2020/0215515 | A1 | 7/2020 | Li et al. |

FOREIGN PATENT DOCUMENTS

| | | | | |
|---|---|---|---|---|
| WO | | 2014202501 | A1 | 12/2014 |
| WO | | 2016049144 | A1 | 3/2016 |
| WO | | 2018005456 | A1 | 1/2018 |
| WO | WO-2018049389 | A1 * | 3/2018 | ............... B01J 38/04 |
| WO | WO-2018157042 | A1 * | 8/2018 | ............ B01J 29/043 |
| WO | | 2018232133 | A1 | 12/2018 |

OTHER PUBLICATIONS

Anene et al., "Experimental Study of Thermal and Catalytic Pyrolysis of Plastic Waste Components", Sustainability, 2018, 10, 3979; doi:10.3390/su10113979. (11 pgs.).
Carey, J., "On the Brink of a Recycling Revolution?", PNAS, Jan. 24, 2017, vol. 114, No. 4, pp. 612-616.
Currao et al., "Understanding Zeolite Frameworks", Department of Chemistry and Biochemistry, University of Bern, 65 pages, 2020.
Elbadawi et al., "Kinetics of oxidative cracking of n-hexane to olefins over VO2/Ce—Al2—O3 under gas phase oxygen-free environment", http://onlinelibrary.wiley.com/doi/10.1002/aic.15491/abstract, 2 pages, Aug. 2016.
Lemonick, S., "Chemistry may have solutions to our plastic trash problem", Pollution, vol. 96, Iss. 25, 9 pages, Jun. 15, 2018.
Olazar et al. "Light olefins from HDPE cracking in a two-step thermal and catalytic process", Chemical Engineering Journal, 207-208 (2012) 27-34, (8 pgs.).
World Economic Forum, Ellen MacArthur Foundation, "The New Plastics Economy—Rethinking the Future of Plastics", http://ellenmacarthurfoundation.org/publications/the-new-plastics-economy-rethinking-the-future-of-plastics, 120 pages, 2016.
Baerlocher, "Atlas of Zeolite Framework Types", Fifth Revised Edition, 2001, 40 pages.
Baerlocher, Ch. et al., "Atlas of Zeolite Framework Types," Sixth Revised Edition, 2007, 404 pages.
Boyadjian, C. et al., Catalytic oxidative cracking of hexane as a route to olefins, 2010, vol. 372, pp. 167-174, Applied Catalysis A: General.
Breck, D.W., General Introduction. Chapter 1, Zeolite Molecular Sieves: Structure, Chemistry, and Use, Wiley, 1974, 28 pages.
Davis, B., "Identification of Molecular Sieve Structures," 1989, pp. 282-347, Van Nostrand Reinhold Catalysis Series.
Fumoto, E., et al., "Production of light oil by oxidative cracking of oil sand bitumen using iron oxide catalysts in a steam atmosphere," 2011, pp. 524-527, vol. 25, Energy Fuels.
Garcia, J.M., et al., "The future of plastics recycling," Nov. 17, 2017, vol. 358(6365), 3 pages, Science.
Ishihara, Y., et al., "Mechanism for gas formation in polyethylene catalytic decomposition," 1992, vol. 33(16), pp. 3482-3486, Polymer.
Karge, et al.,Post-Synthesis Modification I (Molecular Sieves), vol. 1, 2002, pp. 1-54.
Lee, H.W., et al., "Catalytic pyrolysis of polyethylene and polypropylene over desilicated Beta and A1-MSU-F," 2018, vol. 8(501), pp. 1-15, Catalysts.
Manos, G., et al., "Catalytic degradation of high-density polyethylene on an ultrastable-Y zeolite. Nature of initial polymer reactions, pattern of formation of gas and liquid products, and temperature effects," Mar. 25, 2000, vol. 39(5), pp. 1203-1208, Industrial & Engineering Chemistry Research.
Wu, E.L., et al., "New Developments in Zeolite Science and Technology," Murakami, Iijima, Wards, eds, Elsevier, Amsterdam (1986); 547.
Marcilla, A., et al., "Study of the catalytic pyrolysis behavior of polyethylene-polypropylene mixtures," 2005, vol. 74, pp. 387-392, Journal of Analytical and Applied Pyrolysis.
Rahimi, A., et al., "Chemical recycling of waste plastics for new materials production," Jun. 7, 2017, vol. 1, Article 0046, pp. 1-11, Nature Reviews—Chemistry.
Seo, Y-H., et al., "Investigation of catalytic degradation of high-density polyethylene by hydrocarbon group type analysis," 2003, vol. 70, pp. 383-398, Journal of Analytical and Applied Pyrolysis.
Szostak, R., "Molecular Sieves—Principles of Synthesis and Identification," Burtron Davis, ed., Van Nostrand Reinhold Catalysis Series, (1989), 306-312.
Weitkamp, J., et al., "Preparation of oxide, sulfide and other chalcogenide clusters in molecular sieves," 2002, vol. 3, pp. 339-414, Molecular Sieves.
Ding, N. et al., "Effect of hematite addition to $CaSO_4$ oxygen carrier in chemical looping combustion of coal char," Jun. 15, 2015, vol. 5, pp. 56362-56376, RSC Advances, The Royal Society of Chemistry.
Li, H. et al., "Catalytic reduction of calcium sulfate to calcium sulfide by carbon monoxide," Aug. 3, 1999, vol. 38, pp. 3333-3337, Industrial & Engineering Chemistry Research.
Xiao, J. "The diffusion mechanism of hydrocarbons in zeolites," Thesis, Massachusetts Institute of Technology, Jun. 8, 1990, 195 pages.
Non Final Office Action for U.S. Appl. No. 16/888,066, dated Aug. 14, 2020, 27 pages.
Non Final Office Action for U.S. Appl. No. 16/877,992, dated Aug. 7, 2020, 32 pages.
Sofranko et al., "Natural Gas to Gasoline: the ARCO GTG Process", Symposium on Methane Activation, Conversion and Utilization, International Congress of Pacific Basin Societes, Dec. 17-20, 1989, pp. 152-154.
Xu et al., "Combination of $CH_4$ Oxidative Coupling Reaction with $C_2H_6$ Oxidative Dehydrogenation by $CO_2$ to $C_2H_4$", Fuel, 2002, vol. 81, pp. 1593-1597.
Non Final Office Action for U.S. Appl. No. 16/845,815, dated Jun. 17, 2020, 15 pages.
Bovin et al., Electron Microscopy of Oxyborates. I. Defect Structure in the Minerals Pinakiolite, Ludwigite, Orthopinakiolite and Takéuchiite, Acta Cryst., 1981, vol. A37, pp. 28-35.
Kasper et al., "A New Structure Type for Metallic Oxides of Formula $A_6BO_8$", J. Chem. Phys, 1953, vol. 21, pp. 1897-1898.

(56) References Cited

OTHER PUBLICATIONS

Sofronova et al., "Ludwigites: From Natural Mineral to Modern Solid Solutions", Cryst. Res. Technol, 2017, vol. 52, No. 4, 19 pages.

De Vries et al., "The Thermal Decomposition of Potassium and Sodium-Pyrosulfate", J. Inorg. Nucl. Chem., 1969, vol. 31, pp. 1307-1313.

Neal et al., Oxidative Dehydrogenation of Ethane: A Chemical Looping Approach, Energy Technology, 2016, vol. 4, pp. 1-10.

Sofranko et al., "The Oxidative Conversion of Methane to Higher Hydrocarbons", Journal of Catalysis, 1987, vol. 103, pp. 302-310.

Qingjie Guo, Jianshe Zhang & Hongjing Tian (2012) Recent Advances, in CaSO4 Oxygen Carrier for Chemical-Looping Combustion (CLC) Process, Chemical Engineering Communications, 199:11, 1463-1491, DOI: 10.1080/00986445.2012.668591, 30 pages, http://dx.doi.org/10.1080/00986445.2012.668591.

Meng et al., "Manganese Borides Synthesized at High Pressure and High Temperature", Journal of Applied Physics, 2012, vol. 111, 6 pages.

Non Final Office Action for U.S. Appl. No. 17/110,941, dated Feb. 23, 2021, 51 pages.

\* cited by examiner

OXIDATIVE CRACKING OF HYDROCARBONS

CROSS REFERENCE TO RELATED APPLICATIONS

The present application claims priority to and benefit of U.S. Provisional Patent Application No. 62/810,137, filed on Feb. 25, 2019, and U.S. Provisional Patent Application No. 62/810,272, filed on Feb. 25, 2019, the disclosures of both of which are incorporated herein by reference in their entirety for all purposes.

FIELD OF THE INVENTION

The present invention relates to methods, systems, and apparatuses for producing olefins by oxidative dehydrogenation of a hydrocarbon feed.

BACKGROUND OF THE INVENTION

Ethylene and propylene are important building blocks for the petrochemical industry. These olefins are used in the manufacturing of polymers such as polyethylene, polypropylene, polystyrene and many more chemicals of commercial interest. Over 90% of global olefin production may come from the high temperature steam cracking of naphtha or ethane and propane. The steam cracking process, which utilizes furnaces, is highly energy intensive, and 1.5 to 2 tons of carbon dioxide are produced for every ton of olefin product.

Plastics, or polymers, are necessary commodities for daily use with wide-reaching use from healthcare to textile applications. However, plastics production has increased twenty-fold over the last 50 years and much of the waste ends up in the environment and in ever-growing landfills, leading to a mounting ecological problem. Only a small quantity of the 150 million tons per year of plastics such as polyethylene terephthalate (PET), low density polyethylene (LDPE), linear low density polyethylene (LLDPE), high density polyethylene (HDPE), polypropylene (PP), polystyrenes, polyurethanes and polyvinyl chloride (PVC) are recycled to similar quality plastics. These plastics are currently recycled commercially by mechanical processing, i.e., they are sorted, ground up, re-melted, and often extensively purified. This mechanical processing is inefficient and not cost-effective as it requires several expensive, accurate physical process steps to ensure pristine or high-purity plastics. Furthermore plastics recycled using this expensive, laborious process often are still of inferior quality as compared to "virgin" plastics of the same type. Thus, there is a need to develop innovative solutions to address waste disposal and the upcycling of plastics for value-added applications.

Chemical or tertiary recycling or "upcycling", by which is meant returning waste plastics to their monomeric forms for re-processing into new materials (polymeric or not), has regained interest in recent years as an avenue to address the growing waste plastics issue. Well-known plastic chemical or tertiary recycling processes include (1) gasification by converting the waste plastics at high temperature with air or steam to syngas, or (2) pyrolysis by thermally degrading the waste plastics to shorter molecular chains in the absence of air with a catalyst to produce waxes that can be used to make liquid fuels. For example, see Reaction (1) below for the general pyrolysis reaction.

The catalytic cracking of hydrocarbons with acidic catalysts, such as zeolite Y and ZSM-5, is envisioned to proceed via the formation of carbonium ions and the subsequent formation of carbenium ions which lead to rearrangement and cracking of hydrocarbons and the production of hydrogen. For example, such reactions are described in G. Manos, et. al, Ind. Eng. Chem. Res. 39 (2000) 1203-1208. M. M. Wu to Mobil, U.S. Pat. No. 5,079,385, C. S. Lee and M. M. Wu, J. Chem. Soc., Chem Commun., (1985) 250-252, the contents of all which are incorporated by reference herein in their entirety for all purposes. The heat of reaction for these endothermic cracking processes is often supplied by the burning of coke in the catalyst regenerator leading to emissions of carbon dioxide, carbon monoxide and nitrogen oxides. A generalized such reaction scheme is shown below:

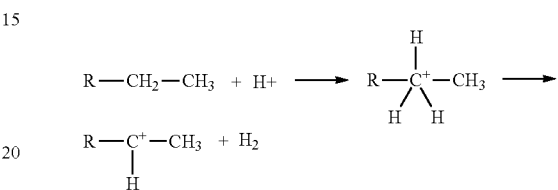

However, these chemical processes cannot handle mixed feeds such as are provided by a waste plastic stream and require high temperatures, leading to poor heat management, expensive fuel costs, and also are a poor choice in terms of environmentally friendly processing. Due to these inefficiencies and high energy requirements, these chemical recycling processes are not used on an industrial scale.

Accordingly, there remains a need for inexpensive and environmentally friendly solutions to address waste disposal and the upcycling of plastics for value-added applications.

SUMMARY OF THE INVENTION

Aspects of the invention relate to methods, systems, and apparatuses for producing olefins by oxidative dehydrogenation of a hydrocarbon feed and in particular feeds that contain mixed plastics.

In accordance with one aspect of the invention, a method is provided for producing one or more olefins by oxidative dehydrogenation, i.e., oxidative cracking, of a hydrocarbon feed in the presence of a metal oxide and a solid acid catalyst, which may be a zeolite. The zeolite is promoted. For example alkali or alkaline earth promoters may modify the acidity of the zeolites, thus reducing over-oxidation and coke formation, during the pyrolysis "cracking" step. These promoters are described in more detail later in this application. In this manner, high yields of desirable olefin and aromatic products are obtained, with minimum oxidation of the hydrocarbon feed to undesired carbon oxides and coke. As will be described below, heat for the endothermic cracking process may be supplied via the conversion of hydrogen to water, as shown in Reactions (1)-(6) below.

(1)

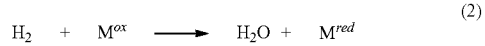

(2)

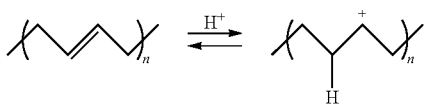

(3)

-continued

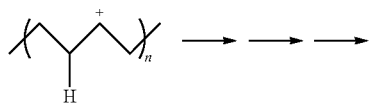

(4)

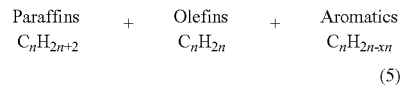

(5)

(6)

Without wishing to be bound by theory, the above series of reactions illustrate the use of the reactor and catalyst technology disclosed herein. In particular, first, plastics are pyrolyzed in the presence of a typical solid acid catalyst (for example, a zeolite or another fluidic catalytic catalyst) as well as the oxidized metal oxide, which is an oxygen transfer agent, to produce hydrogen. This hydrogen then reacts in-situ [Reaction (1)] to reduce the oxidized metal oxide in that is in combination with the solid acid zeolite catalysts ($M^{ox}$) to form water and the reduced form of the metal oxide ($M^{red}$) [Reaction (2)]. Reaction (2) also produces heat, since it is an exothermic reaction. Protonation of the polymer chains produces carbonium ions on the chains [Reaction (3)]. These carbonium ions decompose to paraffins, olefins and aromatics [Reaction (4)]. As used herein, the term paraffin means a mixture of molecules having the general structure of $C_nH_{2n+2}$, i.e., saturated hydrocarbons having a carbon number higher than about 8, but having a smaller average chain length than the polymers that make up the plastic feed. In other words, the paraffins comprise hydrocarbons having a lower weight average molecular weight that the weight average molecular weight of the polymers that comprises the plastics feed. Olefins comprise at least one unsaturation. The reduced metal oxide ($M^{red}$) can be regenerated by oxygen from air (or another source) to produce the re-oxidized metal oxide ($M^{ox}$) and heat [Reaction (6)]. The heat produced by regenerating the metal oxide is used to contribute to the overall process heat requirements and is a key benefit of the present invention.

As shown in Reaction (5), the paraffins may be separated and further oxidatively dehydrogenated by the combination of the solid acid catalyst and the oxidized metal oxide to form olefins, water and the reduced metal oxide (Reaction (5)). The co-product paraffins, when recycled back to the reactor, provide beneficial additional heat for the process as shown in Reactions (5) and (6).

Reaction (5) may also go on at the same time as Reaction (1), meaning that some of the paraffins may also be oxidatively reduced as they are produced.

This cyclic redox concept using a metal oxide in combination with a solid acid catalyst for cracking the feed hydrocarbons, which preferably are in the form of a stream of waste plastics in an oxidative cracking process allows a waste plastics upcycling process having reduced safety risks compared to other technologies by never directly having any gaseous oxidant mix with waste plastics because the reaction scheme as shown above utilizes the metal oxides' reducible lattice oxygen in the pyrolysis reaction. Additionally, the heat management issues of the catalytic pyrolysis processes are avoided as the catalytic material becomes a solid heat-carrier, thus allowing improved heat management and balance through solids transport. In other words, the reactor employing the technology disclosed herein is less prone to developing "hot spots", and may generate at least some of the required process heat without need for the burning of additional fuel, for example.

According to another aspect of the invention, a method is provided for the synthesis of solid acid catalysts for oxidative cracking that contain within their internal lattice structure encapsulated metal oxides that act as oxygen transfer agents that enhance the formation of the desired olefin and aromatic products by minimizing the undesired oxidation of hydrocarbons in favor of the conversion of hydrogen to water. In this way, as described in more detail below, a single solid acid cracking catalyst may be provided to the process for oxidatively cracking a hydrocarbon stream, in which the oxygen transfer agent, i.e. a metal oxide, is encapsulated within the interior structure of a solid acid catalyst, such as a zeolite. Thus, the oxidation of hydrogen to water will be enhanced since the hydrogen can access the interior of the zeolite which contains the oxygen transfer agent, while the exterior of the solid cracking catalyst acid acts to crack the hydrocarbon feed in the pyrolysis step.

Various aspects of the invention may be summarized as follows:

Aspect 1: A method of producing one or more olefins by oxidative dehydrogenation of a hydrocarbon feed having a feed weight average molecular weight, the method comprising a) contacting, in a first vessel, the hydrocarbon feed with:

i) at least one oxidized oxygen transfer agent comprising at least one metal oxide; and b) oxidatively dehydrogenating the hydrocarbon feed at reaction conditions to produce a product stream comprising the one or more olefins and hydrogen;

wherein at least a portion of the at least one oxidized oxygen transfer agent is reduced by the hydrogen at the reaction conditions to produce at least one reduced oxygen transfer agent and water; and c) combining at least a portion of the at least one reduced oxygen transfer agent with a source of oxygen to produce at least a first portion of the oxidized oxygen transfer agent and heat, wherein one or both of the first portion of oxidized oxygen transfer agent and the heat are fed to step a).

Aspect 2: The method according to Aspect 1, wherein the product stream further comprises at least one hydrocarbon having a lower weight average molecular weight than the hydrocarbon feed weight average molecular weight and the at least one hydrocarbon having a lower weight average molecular weight than the hydrocarbon feed weight average molecular weight is fed to step a).

Aspect 3: The method according to either of Aspect 2 and Aspect 3, wherein the one or more olefins comprise at least one of ethylene and propylene.

Aspect 4: The method according to any of Aspects 1-3, wherein the process further comprises the step of:

d) feeding, to a second vessel:

ii) at least a portion of the hydrogen produced in step b); and iii) a gas comprising oxygen;

wherein the portion of the hydrogen and the oxygen are combusted to produce heat that is fed to step a).

Aspect 5: The method according to Aspect 4, wherein the product stream further comprises at least one hydrocarbon having a lower weight average molecular weight than the hydrocarbon feed weight average molecular weight and step d) further comprises feeding, to the second vessel, at least a portion of the at least one hydrocarbon having a lower weight average molecular weight than the hydrocarbon feed weight average molecular weight and combusting the portion of the at least one hydrocarbon having a lower weight average molecular weight than the hydrocarbon feed weight average molecular weight with the oxygen to produce heat that is fed to step a).

Aspect 6: The method according to any of Aspects 1-5, wherein step c) further comprises:
feeding, to a regeneration vessel:
iv) the portion of the reduced oxygen transfer agent; and
v) a gas comprising oxygen;
wherein the portion of the reduced oxygen transfer agent is oxidized to form at least a second portion of the oxidized oxygen transfer agent and the second portion of the oxidized oxygen transfer agent is fed to step a).

Aspect 7: The method according to any of Aspects 1-6, wherein the i) at least one oxidized oxygen transfer agent is in combination with at least one zeolite.

Aspect 8: The method according to Aspect 7, wherein the i) at least one oxidized oxygen transfer agent is encapsulated in inner channels of the at least one zeolite such that access to the encapsulated oxidized oxygen transfer agent is possible only for molecules smaller than the inner channels of the at least one zeolite.

Aspect 9: The method according to Aspect 7, wherein the zeolite has an acid nature and the acid nature of the zeolite is only on the exterior surfaces thereof.

Aspect 10: The method according to Aspect 8, wherein the zeolite has an acid nature and the acid nature of the zeolite is only on the exterior surfaces thereof.

Aspect 11: The method according to any of Aspects 7-10, wherein the at least one zeolite is selected from the group consisting of zeolite Y, ZSM-5, MCM 22, MCM 56, and mixtures thereof.

Aspect 12: The method according to any of Aspects 1-11, wherein the at least one metal oxide comprises a metal oxide selected from the group consisting of oxides of Mn, oxides of Cu, oxides of Ca, oxides of Fe, oxides of La, oxides of Ce, oxides of Pr, oxides of Tb, oxides of Nd, oxides of Dy, and mixtures thereof.

Aspect 13: The method according to any of Aspects 1-12, wherein the at least one oxidized oxygen transfer agent includes at least one oxide of sulfur selected from the group consisting of sulfur dioxide; sulfur trioxide; $CaSO_4$; sulfate salts of Mn, Fe, Sm, Ga, Ti, W, Mo, V, Nb, Cr, K, Cs, Rb, P, Cu, Pb, Ni, and As; and mixtures thereof.

Aspect 14: The method according to any of Aspects 1-13, wherein the at least one oxidized oxygen transfer agent is selected from the group consisting of $MnO_2$, CuO, CaO, sulfur dioxide, sulfur trioxide, $CaSO_4$, and mixtures thereof.

Aspect 15: The method according to any of Aspects 1-13, wherein step a) further comprises contacting the hydrocarbon feed with at least one solid acid catalyst selected from the group consisting of zeolite Y, zeolite A, faujasite, bentonite, sodalite, ZSM-10, MCM-68, MCM-61, MCM-35, ZSM-39, ZSM-23, ZSM-12, SAPO 56, AlPO-5, AlPO-14, AlPO-41, and mixtures thereof.

Aspect 16: The method according to any of Aspects 1-15, wherein step a) further comprises contacting the hydrocarbon feed with at least one fluidic cracking catalyst.

Aspect 17: The method according to any of Aspects 1-17, wherein the hydrocarbon feed comprises at least one polymer having a weight average molecular weight of 1000 Daltons or higher.

Aspect 18: The method according to Aspect 17 wherein the at least one polymer is selected from the group consisting of low density polyethylene, linear low density polyethylene, high density polyethylene, polystyrene, polyethylene terephthalate, poly vinyl chloride, polypropylene, polyurethanes, and mixtures thereof.

Aspect 19: The method according to any of Aspects 1-18, wherein the hydrocarbon feed comprises plastic waste.

Aspect 20: The method according to any of Aspects 1-19, wherein the hydrocarbon feed comprises a mixture of hydrocarbons having an average of at least 7 carbon atoms per molecule.

Aspect 21: The method according to any of Aspects 1-20, wherein the reaction conditions comprise a temperature between 350° C. and 1000° C. and a pressure from 0.9 to 10 atm.

Aspect 22: An apparatus for producing one or more olefins, by oxidative dehydrogenation of a hydrocarbon feed having a feed weight average molecular weight, the apparatus comprising:
a) a first vessel configured and arranged for:
i) contacting the hydrocarbon feed with at least one oxidized oxygen transfer agent comprising at least one metal oxide such that the hydrocarbon feed is oxidatively dehydrogenated at reaction conditions to produce a product stream comprising the one or more olefins and hydrogen;
wherein at least a portion of the at least one oxidized oxygen transfer agent is reduced by the hydrogen at the reaction conditions to produce at least one reduced oxygen transfer agent and water; and the first vessel further being configured and arranged for:
ii) combining at least a portion of the at least one reduced oxygen transfer agent with a source of oxygen to produce at least a first portion of the oxidized oxygen transfer agent and heat, wherein the first portion of oxidized oxygen transfer agent and heat are contacted with the hydrocarbon feed in the first vessel.

Aspect 23: The apparatus according to Aspect 22, further comprising a second vessel configured and arranged for receiving at least a portion of the hydrogen from the first vessel and for receiving a gas comprising oxygen such that a portion of the hydrogen and the oxygen are combusted to produce heat and wherein the second vessel is further configured and arranged to feed the heat to the first vessel.

Aspect 24: The apparatus according to Aspect 23, wherein the second vessel is further constructed and arranged to receive the portion of the reduced oxygen transfer agent from the first vessel and the gas comprising oxygen such that the portion of the reduced oxygen transfer agent is oxidized to form at least a second portion of the oxidized oxygen transfer agent and wherein the second vessel is further configured and arranged to feed the second portion of the oxidized oxygen transfer agent to the first vessel.

Aspect 25: The apparatus according to any of Aspects 22-24, further comprising a separation unit, wherein the separation unit is configured and arranged to receive the product stream from the first vessel and wherein the separation unit is further configured and arranged to produce a light olefin stream comprising at least a first portion of the olefins.

Aspect 26: The apparatus according to any of Aspects 22-25, wherein the at least one oxidized oxygen transfer agent comprising at least one metal oxide is encapsulated in inner channels of at least one zeolite such that access to the encapsulated oxidized oxygen transfer agent is restricted to molecules smaller than a size of the inner channels, the zeolite further having an acid nature and wherein the acid nature of the zeolite is only on the exterior surfaces thereof.

Aspect 27: The apparatus according to Aspects 26, wherein the zeolite is selected from the group consisting of zeolite Y, ZSM-5, MCM 22, MCM 56, and mixtures thereof.

Aspect 28: The apparatus according to any of Aspects 22-27, wherein the at least one oxidized oxygen transfer agent comprises a metal oxide selected from the group consisting of oxides of Mn, CuO, oxides of Ca, oxides of Fe, oxides of La, oxides of Ce, oxides of Pr, oxides of Tb, oxides of Nd, oxides of Dy, and mixtures thereof.

Aspect 29: The apparatus according to any of Aspects 22-28, wherein the at least one oxidized oxygen transfer agent comprises at least one oxide of sulfur selected from the group consisting of sulfur dioxide; sulfur trioxide; $CaSO_4$; sulfate salts of Mn, Fe, Sm, Ga, Ti, W, Mo, V, Nb, Cr, K, Cs, Rb, P, Cu, Pb, Ni, or As; and mixtures thereof.

Aspect 30: A zeolite comprising at least one oxidized oxygen transfer agent encapsulated in inner channels thereof such that access to the encapsulated oxidized oxygen transfer agent is possible only for molecules smaller than the inner channels of the at least one zeolite, the zeolite further having an acid nature and wherein the acid nature of the zeolite is only on the exterior surfaces thereof.

Aspect 31: The zeolite according to Aspect 30, wherein the zeolite is selected from the group consisting of zeolite Y, ZSM-5, MCM 22, MCM 56, and mixtures thereof.

Aspect 32: The zeolite according to either of Aspect 30 or Aspect 31, wherein the at least one oxidized oxygen transfer agent comprises a metal oxide selected from the group consisting of oxides of Mn, oxides of Cu, oxides of Ca, oxides of Fe, oxides of La, oxides of Ce, oxides of Pr, oxides of Tb, oxides of Nd, oxides of Dy, and mixtures thereof.

Aspect 33: The zeolite according to any of Aspects 30-32, wherein the at least one oxidized oxygen transfer agent comprises at least one oxide of sulfur selected from the group consisting of sulfur dioxide; sulfur trioxide; $CaSO_4$; sulfate salts of Mn, Fe, Sm, Ga, Ti, W, Mo, V, Nb, Cr, K, Cs, Rb, P, Cu, Pb, Ni, or As; and mixtures thereof.

BRIEF DESCRIPTION OF THE FIGURES

The invention is best understood from the following detailed description when read in connection with the accompanying drawings, with like elements having the same reference numerals. Included in the drawings are the following figures.

DETAILED DESCRIPTION OF THE INVENTION

The present disclosure provides in one embodiment, selective, regiospecific methods making and using oxygen transfer agents, i.e. metal oxides, and/or oxides of sulfur acting as guests on a host zeolite. The metal oxides and/or sulfur compound may be described herein as regiospecifically encapsulated by the zeolite, by which is understood to mean that the metal oxides and/or oxides of sulfur are guests in the host framework of the zeolite. Importantly, the zeolite itself, even in the form where it is a host for a guest metal oxide and/or oxides of sulfur is capable of acting as solid acid catalyst in the pyrolytic cracking of a hydrocarbon feed, especially if the hydrocarbon feed comprises a polymer or a mixture of polymers, such as a waste plastic stream.

In another embodiment, the oxygen transfer agents may be used in combination with the zeolites as a simple physical mixture.

The present invention for making the encapsulated metal oxides and/or oxides of sulfur can be applied to any framework host material, for example, a zeolite, that has the following properties.

Exchangeable acid (protons) and/or exchangeable base sites (such as alkali metals or ammonium)

Pores, or channels, that lead to cages where clusters of active agents may be formed.

Cages that can accept guest agents, such as metal oxides or compounds comprising oxides of sulfur, in clusters that are at least 2 atoms or greater of the active guest agent.

As used herein, the terms "guest agent" or "active agent" or "active guest agent" should be understood as referring to the oxygen transfer agent, i.e. a metal oxide, and/or compounds comprising oxides of sulfur which may or may not be a guest, or encapsulated, in a host framework.

Figure 1:
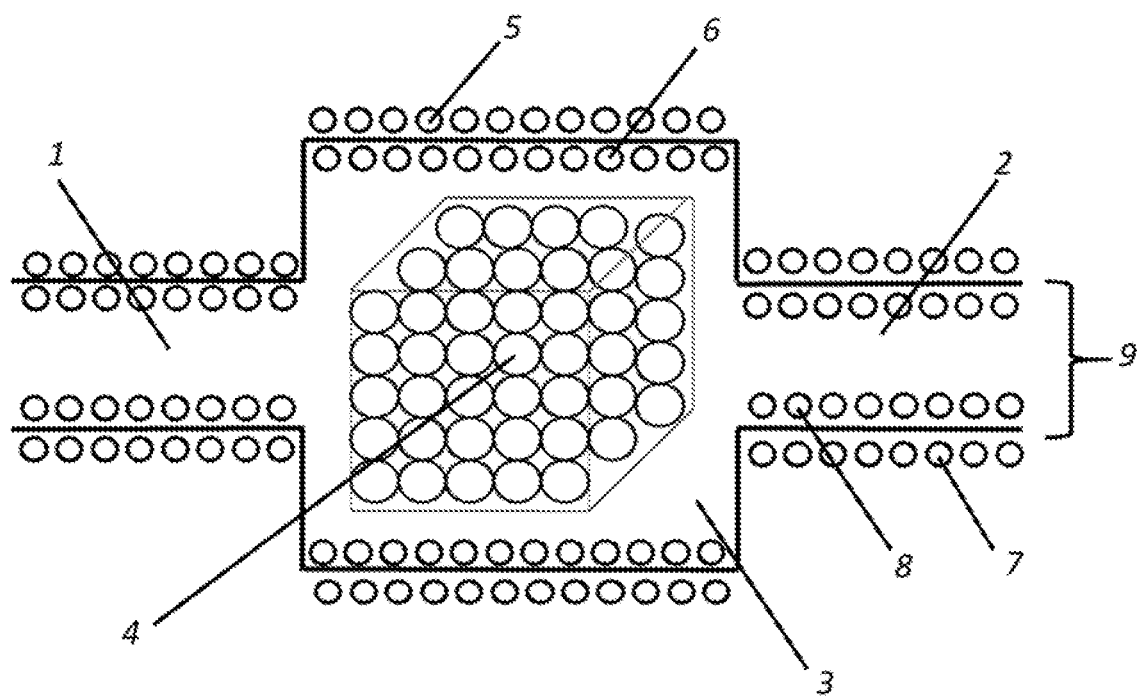
FIG. 1 illustrates an encapsulated metal oxide produced by the methods of the present invention.

FIG. 1 illustrates a schematic representation of an example of an oxygen transfer agent hosted in a zeolite framework according to certain aspects of the present invention. In this example, the oxygen transfer agents are guests in zeolites that have been regioselectively modified. The zeolites that are to be regioselectively modified to produce the encapsulated oxygen transfer agents according to the present invention may have channels, 1 and 2, leading to cages, 3, where the size of the channels 1, 2 is between 3 and 8 Angstroms, and the cages 3 are larger than the channels 1,2 in order to encapsulate clusters of active agents (i.e. the metal oxide oxygen transfer agents) as guests, 4. The host also has external exchangeable sites 5 and 7, and internal exchangeable sites, 6 and 8. As generally known in the art, since these hosts are zeolites, these sites have the general formula of M-O-M* where M is typically Al or Si and M* is typically H, Na, K, Ca or any ionic material that balances the charge of the zeolitic framework. Additionally, M* may be a cationic metal that is useful to promote desired reactions. Synthetic methods, as known in the art may be used to form guest clusters of the active agents in the form of the oxygen transfer agents, 4, inside the host cages. For example, H. G. Karge, et. al., *Post-Synthesis Modification I (Molecular Sieves)*, Vol. 1, (2002) 1-54 the disclosure of which is incorporated by reference herein in its entirety for all purposes describes such synthetic methods.

While all the aforementioned synthesis of host-guest systems is known, we now have invented a method to regiospecifically distribute the M* cations throughout the host. Taking advantage of the unique channel diameter of the host zeolites, the oxygen transfer agents may regiospecifically exchange M* guests at locations of choice on the host.

As an example of the present invention, copper nitrate may be exchanged into, and onto, the sodium form of zeolite Y. As is known in the art, and shown in FIGS. 1-3, clusters 4 of copper may formed in the cage 3.

In another embodiment, depending on the desired use of the guest-host system, it may be desirable to have all of the external exchangeable sites of the host, 5 and 7, be primarily in the form of protons, i.e., be acidic, while maintaining the internal exchangeable sites, 6 and 8, as copper as described above. In this way, the host zeolite encapsulating the oxygen exchange agent is uniquely able to regiospecifically participate in two separate reactions in the oxidative cracking of a hydrocarbon. Due to steric hindrance, the larger hydrocarbon chains are unable to interact with the oxygen transfer agent that is a guest in the host zeolite. Thus, the larger hydrocarbons will not over-oxidize, which results in undesirable reaction products such as coke. However, the hydrogen is not so constrained and may easily diffuse into the zeolite host, and reduce the oxidized oxygen transfer agent, producing water in highly exothermic reaction. Meanwhile, the exterior of the zeolite acts as the solid acid catalyst and donates protons in the cracking of the hydrocarbon.

In a method of the present invention, this second regiospecific exchange may be accomplished by contacting the an alkali or alkaline earth form of for example, zeolite Y, in suitable methods known in the art, with a bulky ammonium salt. For this example, tri-n-butyl ammonium chloride is employed for this purpose. This salt is too large to travel into the zeolite channel and exchange with the internal sodium cations. This is shown schematically in FIG. 2, wherein the tetrahedron represents any molecule too large to enter the channels 1, 2. Other non-limiting examples of such salts are those wherein the static adsorption of the unprotonated species on the zeolite is less than 0.010 um3/g. See R. Szostak, "Molecular Sieves, Principles of Synthesis and Identification", Burtron Davis, ed., Van Nostrand Reinhold Catalysis Series (1989), 306-312, and E. L. Wm, G. R. Landolt, A. W. Chester, "New Developments in Zeolite Science and Technology", Murakami, Iijima, Wards, eds, Elsevier, Amsterdam (1986); 547. Nonlimiting examples are salts are those having the formula $HY(RR_1R_2)X$; wherein Y is a Group 5a element, preferably N, P, As, Sb, Bi, and the like; X is halide, preferably Cl; and R, $R_1$ and $R_2$ are alkyl groups, preferably having 3 or more carbon atoms or aryl groups. Other details of making these proton exchanged zeolites having an acid nature wherein the acid nature is only on the outside thereof are disclosed in U.S. Pat. No. 5,091,163, the contents of which is incorporated by reference herein in its entirety for all purposes.

In a subsequent step, also known in the art, the zeolite thus exchanged with the bulky ammonium salt may be calcined at a high enough temperature to drive off the amine moiety and produce a regiospecificly protonated form of H-zeolite Y such that the acid nature of the zeolite is only on the exterior surfaces thereof. This zeolite may then have the alkali or alkaline earth sites remaining in the interior exchanged with the oxygen exchange agent, such as a metal oxide, and thus the oxygen exchange agent is hosted on the interior thereof. This twice-exchanged zeolite may then be calcined again.

In certain embodiments, these two exchange and then calcining steps may be performed in either order; i.e., the oxygen exchange agent may be exchanged with the zeolite, the zeolite calcined; and then the zeolite may be subsequently exchanged with the bulky salt and calcined again to produce the zeolite in which the acid nature of the zeolite is only on the exterior thereof and the oxygen exchange agent is hosted on the interior thereof. Furthermore, in certain embodiments, the intermediate calcining step is optional. The two exchanges may be performed in either order without doing the calcining step after the first exchange. The zeolite would be calcined only once, after both exchange steps have been performed.

While not wanting to be limited to any particular reaction chemistry or theory, an example of an effective use of the aforementioned example would be for the oxidative dehydration of hydrocarbons, particularly C4 and higher hydrocarbons, and especially for hydrocarbons comprising polymers. In this example, the external proton, acidic, sites of the zeolite could effectively promote the cracking of large molecules to smaller molecule olefins and hydrogen.

For simplicity, the cracking is shown as reaction A below. However, this concept may be extended to cracking more complex organic mixtures, for example, but not limited to naphtha and mixed plastics.

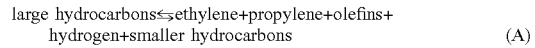

Figure 2:
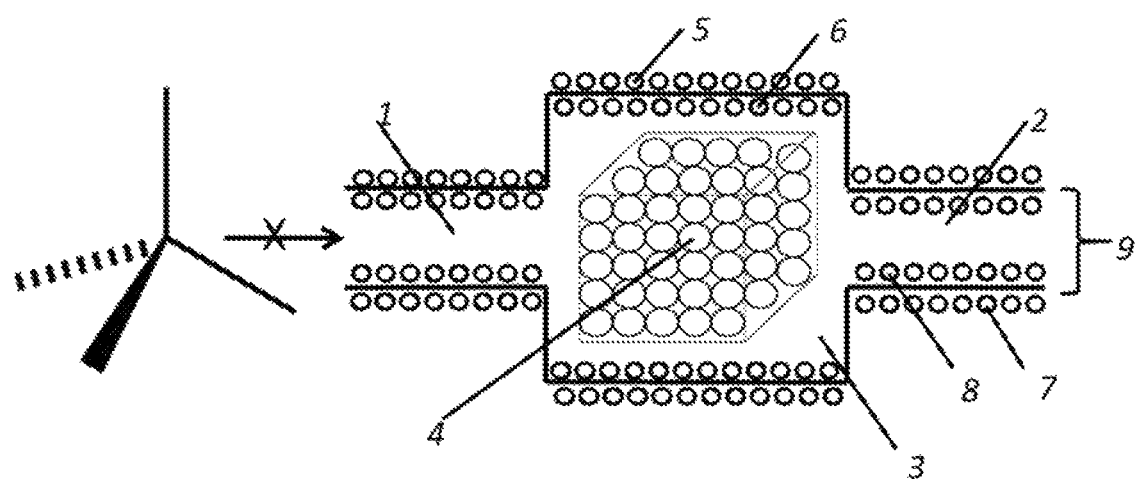
FIG. 2 illustrates how the surface of the catalyst can be modified by bulky agents during catalyst synthesis and also how large molecules are protected from over oxidation by the encapsulated metal oxide.

The large hydrocarbon, for example a hydrocarbon having a chain length of at least 6 or higher and preferable much larger, such as a paraffin or a polymer, represented in this example by the tetrahedron in FIG. 2, will diffuse very slowly, or not at all through the narrow, ~4.5 Angstrom, channels 1 and 2 of zeolite Y as shown in FIG. 2. The tetrahedron in FIG. 2 is understood to represent any molecule too large to enter the channels 1 and 2. Reference number 9 in FIGS. 2 and 3 indicates generally where the channels 1 and 2 are measured. This non-diffusion, or very slow diffusion is represented by the arrow that is crossed out with an X in FIG. 2. Accordingly, these larger molecules preferentially interact with and are cracked by the acid sites on the surface of the zeolite, rather than being oxidized by the oxygen transfer agents 4, which are guests in the host zeolite. However, smaller olefins and certainly hydrogen will diffuse through the channels 1 and 2, and into the cages of the zeolite, as shown schematically in FIG. 3. The benefit of the present invention, as described in the aforementioned example, is to focus the acid cracking chemistry on the exterior of the zeolite and limit the formation of coke from olefins that reach the internal channel and cages. In this example, the guest metal oxide cluster, 4, could very effectively react with hydrogen to produce water and thereby the oxide is reduced, as shown in Reaction 2. This means that access to the encapsulated oxygen transfer agent is possible only for molecules that are smaller than the inner channels of the host zeolite. For example, the size of these inner channels as shown by reference number 9 in FIGS. 1-3 may be from 3.0 to 7.0 Angstroms, preferably 4 to 5 Angstroms with framework densities between 12 to 21. The size of the inner channels may be from 3.0 to 4.5, or from 4.0 to 7.0, or from 3.0 to 5.0, or from 3.0 to 8.0 Angstroms. The framework definition is defined as number of T-atoms/1000 Angstroms; i.e. any zeolite with fully crosslinked frameworks. T-atoms are those that are tetrahedrally coordinated in the zeolite, for example, Si, Al, P, As, Ga, Ge, B, Be, etc. The hydrocarbon feed is cracked and dehydrogenated by oxidative dehydrogenation, i.e. oxidative cracking, using an oxygen transfer agent comprising a metal oxide and/or a compound comprising oxides of sulfur, e.g., $SO_2$, $SO_3$, $CaSO_4$, as further discussed below. Oxidative dehydrogenation mechanisms may occur according to the following generalized formula of Equation 1:

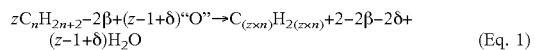

where z=the number of reacting molecules; n=the number of carbon atoms in the reacting molecule; β=the degree of unsaturation where the value is zero for single bonds, one for double bonds and molecular rings, and two for triple bonds; and δ=the change in the degree of unsaturation. "O" represents an oxygen source. The metal oxide and/or an oxide of sulfur may be used in methods, systems, or apparatuses discussed herein as a catalyst, which promotes catalytic use of molecular oxygen, or as a reducible agent, which has been oxidized, to provide an oxygen atom to oxidize the alkanes of the hydrocarbon feed.

The reduced metal oxide, in this example, could be re-oxidized with oxygen which may be a co-feed with the hydrocarbon reactants or could be re-oxidized in a separate cycle, such as a regeneration unit whereby the metal oxide agent is re-oxidized in the substantial absence of hydrocarbon. Therefore, a particularly useful application of this example, and the present invention is the oxidative cracking of naphtha boiling range molecules and plastics to convert them to ethylene, propylene, butylenes and other useful products. A non-limiting example of such a use of this catalyst, i.e., a combination of the oxygen transfer agent (a metal oxide and/or an oxides of sulfur) and a solid acid catalyst is described below. The combination of the oxygen transfer agent and a solid acid catalyst may be a guest-host combination, or may be a simple physical mixture.

Figure 3:
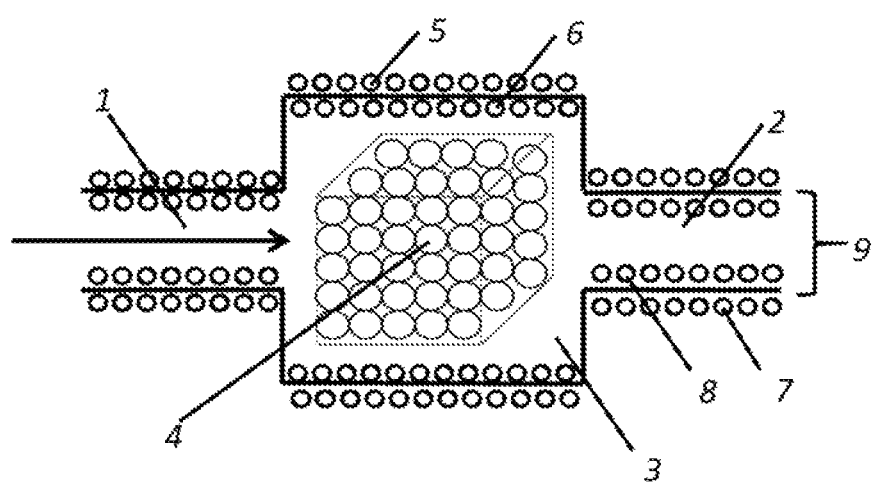
FIG. 3 illustrates how small molecules, such as hydrogen, can selectivity access and reduce the encapsulated metal oxide.

The oxygen transfer agent, which may be encapsulated, as described above, i.e., as the guest in a host catalyst, as shown in FIGS. 1-3, or may be a simple physical mixture is such that minimum hydrocarbon oxidation occurs and high hydrogen conversion to water is favored. In this manner, high yields to desirable olefin and aromatic products are obtained, with minimum oxidation to undesired carbon oxides and heat for the endothermic process is supplied via the conversion of hydrogen to water, as shown in Reactions (1)-(6) below.

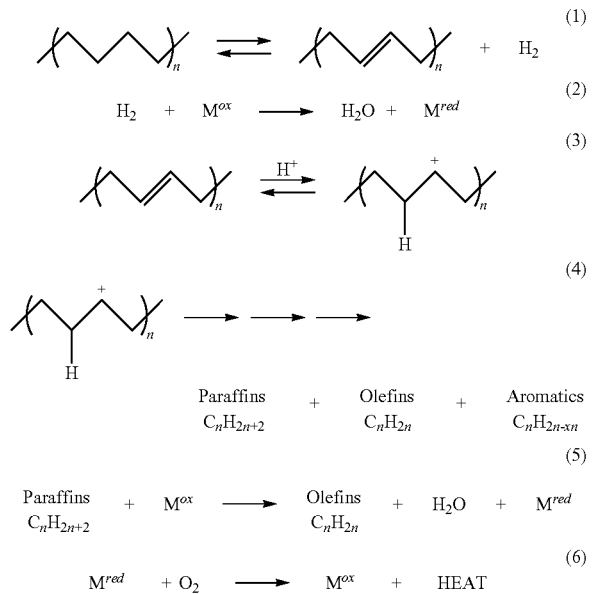

Without wishing to be bound by theory, the above series of reactions illustrate a proposed series of reactions that may occur in a reactor with use of the oxidative cracking catalyst technology disclosed herein. In particular, first, hydrocarbons, such as waste plastics, are pyrolyzed in the presence of a catalyst to produce hydrogen [Reaction (1)]. This catalyst is preferably a solid acid catalyst, but does not have to be. At least some of the hydrogen may be used in-situ to reduce the oxidized metal oxide ($M^{ox}$) to form water and the reduced form of the metal oxide ($M^{red}$) [Reaction (2)]. The reduction of the oxidized metal oxide and the concomitant production of water helps drive the pyrolysis, providing both the necessary heat of reaction and driving the equilibrium of Reaction (1) to higher conversion. Protonation of the polymer chains by the solid acid that may be in combination with the metal oxide produces carbonium ions on the chains [Reaction (3)]. These carbonium ions decompose to paraffins, olefins and aromatics [Reaction (4)]. As used herein, the term paraffin means molecules having the general structure of $C_nH_{2n+2}$, i.e., saturated hydrocarbons, that have a weight average molecular weight that is lower than the weight average molecular weight of the feed stream hydrocarbons. Olefins comprise at least one unsaturation. The reduced metal oxide ($M^{red}$) can be regenerated by oxygen from air (or another source) to produce the re-oxidized metal oxide ($M^{ox}$) and heat [Reaction (6)]. This heat may be used to drive the process.

As shown in Reaction (5), the paraffins may be separated and further oxidized by the oxidized metal oxide to form olefins, water and the reduced metal oxide catalyst (Reaction (5)). The paraffin may be separated and recycled back as feed to Reaction (1).

This cyclic redox concept in an oxidative cracking process allows a waste plastics upcycling process to significantly reduce safety risks by never directly having any gaseous oxidant mix with waste plastics because the reaction scheme as shown above utilizes the oxygen transfer agents' reducible lattice oxygen due to the reduction of the oxidized oxygen transfer agent. Additionally, the heat management issues of the catalytic pyrolysis processes are avoided as the catalytic material becomes a solid heat-carrier, thus allowing improved heat management and balance through solids transport. In other words, the reactor employing the technology disclosed herein is less prone to developing "hot spots", for example.

The present invention may be applied to any reaction, or catalytic system, where a metal oxide, or compounds comprising oxides of sulfur, guest resides as a cluster inside a zeolite host. For example, calcium sulfate may be used as an oxygen transfer agent in certain embodiments. The present invention allows for regiospecific location of cations in the zeolite, either protons or other metal cations. In addition to the aforementioned example using sodium, the cation may be any alkaline metal, alkaline earth metal, transition metal or rare earth metal as long as it may supply the positive charge required in the zeolite framework. Therefore, after using the methods of the present invention to regiospecifically adjust the internal acidity or basicity of the zeolite, the external surface could be decorated with other metals, such as transition metals, using bulky salts of these metals.

In certain embodiments, these metal oxides may be encapsulated, i.e., are guests in the host zeolitic materials disclosed herein and thus may be used as oxygen transfer agents, or as true catalysts, in any application where the oxidation of the feed to useful products needs to be separated from an area on a zeolite that has Brönsted or Lewis acid acidity. The metal oxides and/or compounds comprising oxides of sulfur may be used with zeolites as a simple mixture, in another embodiment. Useful applications include but are not limited to:

The oxidative dehydration (ODH) of alkane to alkenes such as ethane to ethylene, propane to propylene, butane to butylenes or similar ODH reactions The catalytic cracking of large hydrocarbons in parallel with hydrocarbon dehydrogenation. This may be particularly useful in the processing of light oil, or tight oil, from shale oil as demonstrated in reactions (1)-(6) above, as well as the process of "upcycling" a plastics waste stream. An added benefit is the formation of valuable light olefin products such as ethylene, propylene, butylenes and amylenes. In this case, the in-situ conversion of hydrogen to water provides useful heat for the cracking process.

The catalytic cracking ("upcycling") of plastics, and plastic waste, as discussed in detail above.

In the case where common plastic waste such as polyethylene, polypropylene, polystyrene, PETE, PVC and others is destined for a landfill, according to certain embodiments of the present invention, the plastic may instead be converted to high value olefin monomers, as shown in Reactions (1)-(6), above. An added benefit, as discussed above with respect to Reactions (1)-(6) is the formation of valuable light olefin products such as ethylene, propylene, butylenes and amylenes from plastics. In this case, the in-situ conversion of hydrogen to water provides useful heat for the plastic waste cracking process. In addition to the oxidative dehydrogenation cracking of saturated hydrocarbons to less saturated hydrocarbons, the oxygen transfer agents, in the form of the metal oxide regiospecifically exchanged zeolites described herein, are capable of performing oxidative dehydrogenation cracking of hydrocarbons having a larger carbon chain (e.g., a higher weight average molecular weight) to hydrocarbons having a shorter carbon chain (e.g., a lower weight average molecular weight). As one example, Reactions (7) and (8) show the oxidative dehydrogenation cracking reactions of hexane to ethylene.

$$C_6H_{14} + \tfrac{1}{2}O_2 \rightarrow 3C_2H_4 + H_2O \quad (7)$$

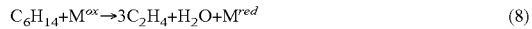

$$C_6H_{14} + M^{ox} \rightarrow 3C_2H_4 + H_2O + M^{red} \quad (8)$$

The metal oxide ($M^{ox}$) utilized as the oxygen transfer agent comprises oxygen and at least one metal, preferably at least one element selected from the group consisting of copper (Cu), manganese (Mn), iron (Fe), lanthanum (La), cerium (Ce), praseodymium (Pr), terbium (Tb), neodymiun (Nd), and dysprosium (Dy). The metal oxides may be used as commonly mined mixtures, such as didymium. Preferably, the metal oxide comprises Pr and any compounds, complexes, composites, or the like thereof. The oxygen transfer agent may be comprised of at least 0.5% by weight metal oxide(s) and up to 100% by weight metal oxide(s). For example, the oxygen transfer agent may comprise an amount, by weight, of metal oxide ranging from 5% to 95%; preferably 15% to 90%; more preferably 20% to 85%; more preferably 25% to 80%; more preferably 30% to 75%; more preferably 35% to 70%; and/or more preferably 40% to 65% by weight. Additionally and/or alternatively, the oxygen transfer agent may comprise an amount of metal oxide, by weight, ranging from 0.5% to 10%; 10% to 20%; 20% to 30%; 30% to 40%; 40% to 50%; 50% to 60%; 60% to 70%; 70% to 80%; 80% to 90%; or 90% to 100%. Mixtures of different metal oxides may also be utilized. The oxygen transfer agent may include at least one promoter integrally dispersed (e.g., uniformly dispersed) within the metal oxide. In one embodiment, the promoter is selected from the group consisting of sodium (Na), lithium (Li), calcium (Ca), magnesium (Mg), strontium (Sr), and barium (Ba).

The oxygen transfer agent may also comprise compounds comprising oxides of sulfur. Non-limiting examples include $SO_2$, $SO_3$, $CaSO_4$, sulfate salts of Mn, Fe, Sm, Ga, Ti, W, Mo, V, Nb, Cr, K, Cs, Rb, P, Cu, Pb, Ni, or As.

The oxygen transfer agent may also further comprise a zeolite that may be configured to accelerate the rate of oxidative dehydrogenation cracking of a hydrocarbon feed. Preferably, the zeolite has a composition in accordance with the general formula: $M_{2/n}O \cdot Al_2O_3 \cdot ySiO2 \cdot wH_2O$ where y is from 2 to 1,000,000,000, M is a positively charged element for balancing the charge of the zeolite and may include protons, alkaline metals, alkaline earth metals or other elements known to those skilled in the art, n represents the cation valence and w represents the number of water molecules per zeolite unit structure, such that, at least 5% of n are protons. For example, the zeolite may have a composition in accordance with the above general formula where y is from 4 to 35. In one embodiment, the zeolite comprises ZSM-5, while in another embodiment the zeolite is selected from a group consisting of sodium form of zeolite Y, ZSM-5, MCM 22, and MCM 56. Suitable amounts of Brönsted and/or Lewis acids may be utilized to optimize the activity of the zeolites. The molar ratio of the amount of metal oxide(s) to zeolite(s) may range from, e.g., 100:1 to 1:100; 95:5 to 5:95; 90:10 to 10:90; 85:15 to 15:85; 80:20 to 20:80; 75:25 to 25:75; 70:30 to 30:70; 65:35 to 35:65; 60:40 to 40:60; and/or 55:45 to 45:55. Additionally and/or alternatively, the molar ratio of the amount of metal oxide(s) and/or oxides of sulfur to zeolite(s) may range from ranging from 95:5 to 90:10; 90:10 to 85:15; 85:15 to 80:20; 80:20 to 75:25; 75:25 to 70:30; 70:30 to 65:35; 65:35 to 60:40; 60:40 to 55:45; 55:45 to 50:50; 50:50 to 45:55; 45:55 to 40:60; 40:60 to 35:65; 35:65 to 30:70; 30:70 to 25:75; 25:75 to 20:80; 20:80 to 15:85; 15:85 to 10:90; or 10:90 to 5:95.

The aforementioned metal oxide and/or compounds comprising oxides of sulfur may be guests (or encapsulated) in a host framework of the aforementioned zeolite(s), or the zeolites(s), i.e., the metal oxide(s) as oxygen transfer agents may be guests in a host system, such as a zeolite Y, as described above. Alternatively or in addition, the metal oxide(s) disclosed may be utilized as a simple physical mixture with the zeolite(s).

The oxygen transfer agents, whether or not encapsulated in the host as disclosed herein may be prepared by any methods known by those skilled in the art, including, but not limited to, precipitation, co-precipitation, impregnation, granulation, spray drying, dry mixing, etc. Precursors may be transformed into active agents by calcination at temperatures suitable for the formation of the active components, e.g., in the range of 400° to 1,100° C. The calcination may be performed under any atmosphere, such as air, inert gases, hydrogen, carbon monoxide, and hydrocarbon gases, so as to form the active oxygen transfer agents of the present invention. The oxygen transfer agent may be admixed or otherwise formulated with binders, supports, carriers and the like using any conventional procedures known in the art and may be utilized in any suitable shape or physical form such as powder, granules, pellets, beads, rings, monoliths, extrudates and the like. Suitable oxygen transfer agents and methods of manufacturing the same may be found in PCT Patent Application no. PCT/US17/39448, which is incorporated herein in its entirety for all purposes.

Solid acid catalysts suitable for use in the practice of this invention include but are not limited to zeolite Y, zeolite A, faujasite, bentonite, sodalite, ZSM-10, MCM-68, MCM-61, MCM-35, ZSM-39, ZSM-23, ZSM-12, SAPO 56, AlPO-5, AlPO-14, AlPO-41 and other zeolites as known to those skilled in the art. Fluidic catalytic cracking catalysts that may be used in the practice of this invention may include, but are not limited to zeolite Y and lanthanum stabilized zeolite Y.

For avoidance of doubt, the zeolite that is in combination with (i.e., encapsulating or mixed with) the oxygen transfer agent may be one and the same as the solid acid catalyst and/or the FCC catalyst. In other embodiments, the solid acid catalyst and/or the FCC catalyst may be an additional component.

Figure 5:
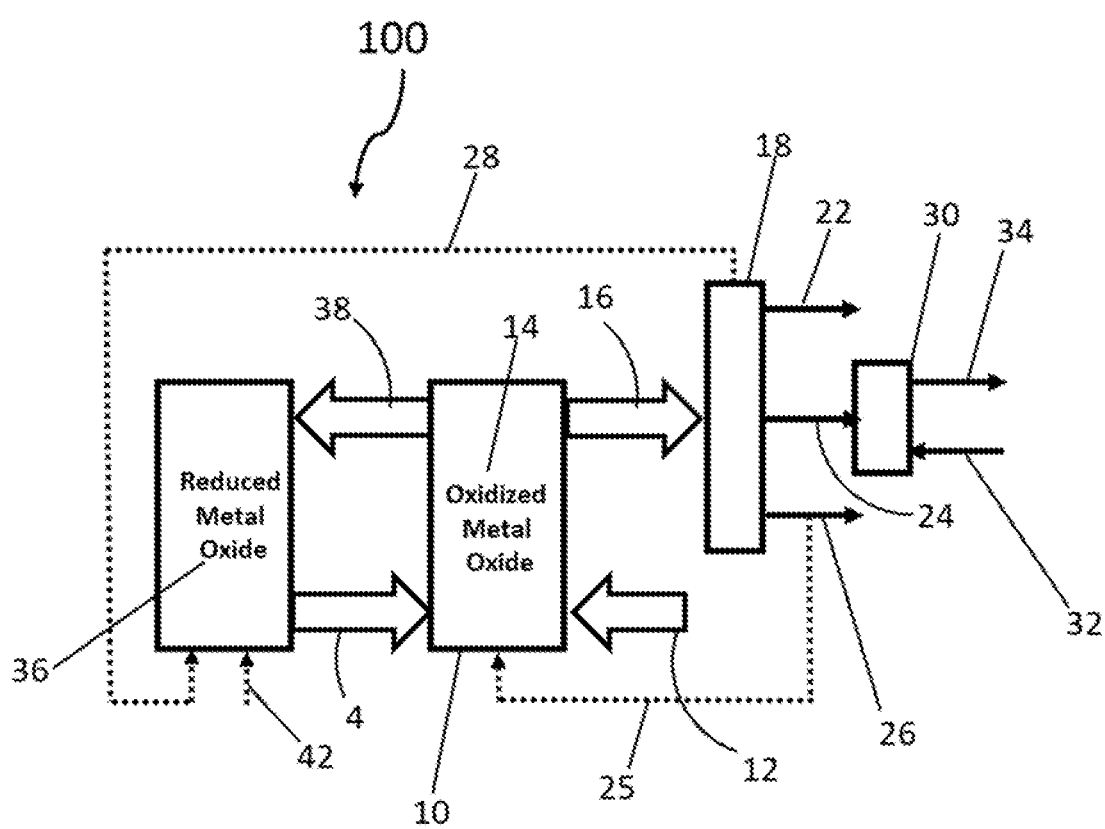
FIG. 5 is a simplified schematic block diagram of a reactor and process in accordance with aspects of the invention.

FIG. 5 is a schematic of an exemplary, non-limiting system 100 for the oxidative cracking of a hydrocarbon feed comprised of hydrocarbon feed having with a carbon number greater than six. A non-limiting example of such a feed is a polymer, or plastic, or mixtures of various types of polymers, having a weight average molecular weight greater than 1000 g/mol as measured with gel permeation chromatography. Mixed pentanes, mixed hexanes and higher hydrocarbons are also suitable as feeds, as are paraffin and oligomeric hydrocarbons. While not limited in the commercial application of the present invention, the process system of FIG. 5 demonstrates an effective process to integrate the methods of this invention. This method could be employed as a stand-alone processing unit or may be integrated into existing petrochemical complexes.

As shown in FIG. 5, a reaction system apparatus 100, comprises, consists of or consists essentially of a reactor 10. A hydrocarbon feed 12, which may comprise waste plastic, is fed to the reactor 10, which contains a metal oxide oxygen transfer agent comprising at least the oxidized metal oxide $M^{ox}$ 14 as an oxygen transfer agent. The oxygen transfer agent may additionally or alternatively be a compound comprising oxides of sulfur. A zeolite and/or an FCC catalyst and/or a solid acid catalyst may also be present in the reactor 10. The oxygen transfer agent 14 may be a guest in a host framework, which may be a zeolite. The reactor 10 is constructed and arranged such that the feed 10 is pyrolyzed (i.e., dehydrogenated) at a temperature of 350° C. to 1000° C., to form a double bond in the hydrocarbon feed or polymer chain and produce hydrogen, as shown in Reaction (1). This hydrogen reacts with the oxidized metal oxide $M^{ox}$ to produce water and to reduce the oxidized metal oxide $M^{ox}$ 14 to $M^{red}$ 18 as shown in Reaction (2). By protonation of the double bond by the solid acid, shown in Reaction (3), polymer or hydrocarbon chains from the plastic waste stream 12 produce carbenium ions. These carbenium ions decompose to form a product stream 16 which comprises materials having a lower weight average molecular weight than the feed stream 12 components' weight average molecular weight. Non-limiting examples of such materials that comprise stream 16 are, for example, methane, ethane, hydrogen, paraffins, C4 and C5 hydrocarbons, aromatics, and olefins, including ethylene and propylene, shown in Reaction (4).

The product stream 16, may fed to a separations unit 18. The separations unit 18 is constructed and arranged so as to be capable of producing at least two streams, or as shown in FIG. 5, may optionally produce four streams 22, 24, 26, 28. Stream 22 is a light olefin stream and comprises at least the ethylene and propylene. Stream 24 comprises the C4 and C5 hydrocarbons, stream 26 comprises other, heavier products, comprising hydrocarbons having a lower weight average molecular weight than the feed hydrocarbon weight average molecular weight (sometimes referred to as a paraffin stream), and stream 28 is comprises methane and ethane, as well as hydrogen. As can be seen in FIG. 5, stream 24 may be optionally sent to a second reactor 30 where the C4 and C5 are reacted with methanol and/or ethanol 32 to produce a mixture 34 comprising at least one of methyl tert-butyl ether, tert-amyl butyl ether, ethyl tert-butyl ether, or tert-amyl ethyl ether.

Associated with the reactor 10 may be a regeneration unit 36. As can be seen in FIG. 5, when the feed 10 is pyrolyzed in the reactor 10, the oxidized metal oxide $M^{ox}$ 14 is converted to the reduced metal oxide $M^{red}$ 38. The reduced metal oxide $M^{red}$ 38 is fed to the regeneration unit 36 where it is contacted with an oxygen-containing stream 42, preferably air, to oxidize the reduced metal oxide $M^{red}$ 38 to the oxidized metal oxide $M^{ox}$ 14, as shown in Reaction (6). The oxidized metal oxide $M^{ox}$ 14 is fed back to the reactor 10 in stream 42. The oxidation is an exothermic reaction and thus heat is also transferred back to the reactor 10. The stream 28 comprising methane, ethane and hydrogen, emerging from the separation unit 18 may be fed back to the regeneration unit 36 and combusted to provide fuel to heat the reactor 10. Although not shown in FIG. 5, in another embodiment, stream 28 may be fed back to the reactor 10. In this way, additional heat may be generated, due to the formation of water by the hydrogen reducing the oxidized metal oxide $M^{ox}$ 14. This heat is generated without combustion of oxygen the undesirable formation of carbon dioxide.

As shown in FIG. 5, at least a portion 25 of the stream 26, which comprises generally the heavier components of the product stream 16 may be recycled back the reactor 10 to react further with the oxidized metal oxide $M^{ox}$ 14 to contribute to product stream 16, as well as produce water and the reduced metal oxide $M^{red}$ 38 as shown in Reaction (5).

Suitable hydrocarbon feeds that may be employed in the practice of this invention include but are not limited to mixed hydrocarbons having an average carbon number of 5 or above, or above 6, or above 7, or above 8, or above, 9 or above 10 carbons, or even higher. Also suitable are mixed plastics or polymers, having a weight average molecular weight of 1000 Da or higher, as measured by gel permeation chromatography and polystyrene standards. The hydrocarbon feed, particularly if it contains waste plastic, may have a weight average molecular weight in Daltons as measured by gel permeation chromatography with polystyrene standards of at least 1000, or 5000, or 10,000, or 25,000, or 50,000, or 100,000 Daltons.

Plastics and mixtures of plastics, such as those arising from plastic recycling efforts are suitable to use as hydrocarbon feeds in embodiments of the present disclosure. Non-limiting examples include: polyethylene terephthalate (PET), light low density polyethylene (LDPE), linear low density polyethylene (LLDPE), high density polyethylene (HDPE), polypropylene (PP), polystyrenes, polyurethanes, polyvinyl chloride (PVC), copolymers of any of all of these, and mixtures thereof. The hydrocarbon feed may additionally comprise substances and/or polymers that contain elements in addition to carbon and hydrogen, for example polyurethane, polyvinyl chloride, and/or other such plastics as are known to be included in a recyclable plastics waste stream, especially a stream comprised of a mixture of plastics.

Suitable reaction conditions for the oxidative cracking of the hydrocarbon feed are for example temperatures from 300° C. to 1000° C., 350° C. to 1000° C., 400° C. to 1000° C., 400° C. to 800° C., or from 500° C. to 700° C. In one preferred embodiment, the temperature may be from 550° C. to 650° C. where conversion is observed to be higher than non-catalytic pyrolysis at a similar temperature. Pressure may be from sub-atmospheric to super-atmospheric with a range of 0.1 to 100 atm. In other embodiments, the pressure range may be 0.9 to 10 atm. Other pressure ranges may be from 0.9 to 1.5, 0.5 to 2, 0.9 to 5, 0.9 to 7, or 0.9 to 1.1 atm.

EXAMPLES

The following examples are non-limiting embodiments of the present invention, included herein to demonstrate the advantageous utility obtained from aspects of the present invention.

Example 1. (Comparative)

Figure 4:
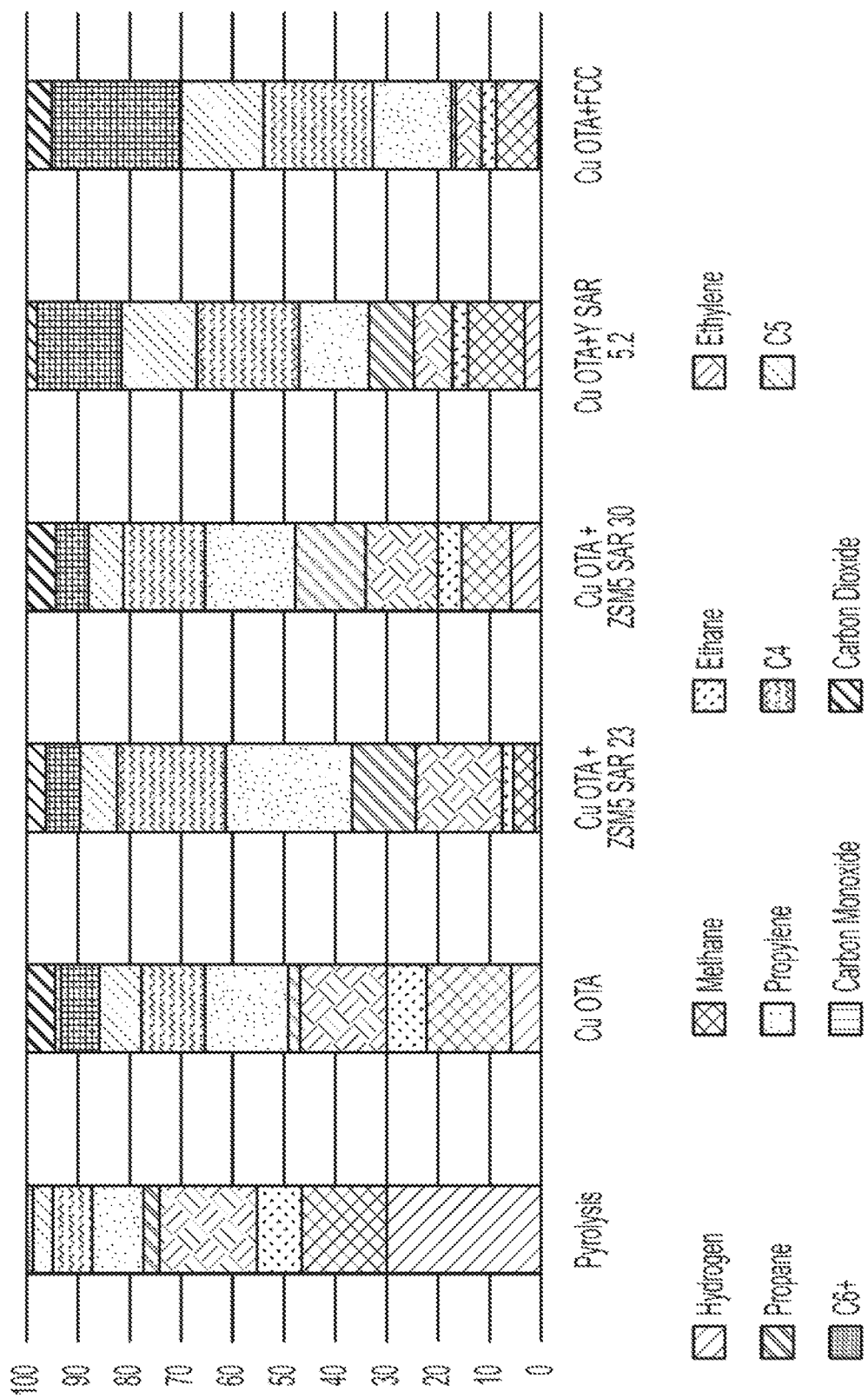
FIG. 4 is a graph illustrating how the combination of solid acids and metal oxides convert plastics to higher yields of olefins than pyrolysis or catalytic cracking in the absence of a metal oxide.
Figure 6:
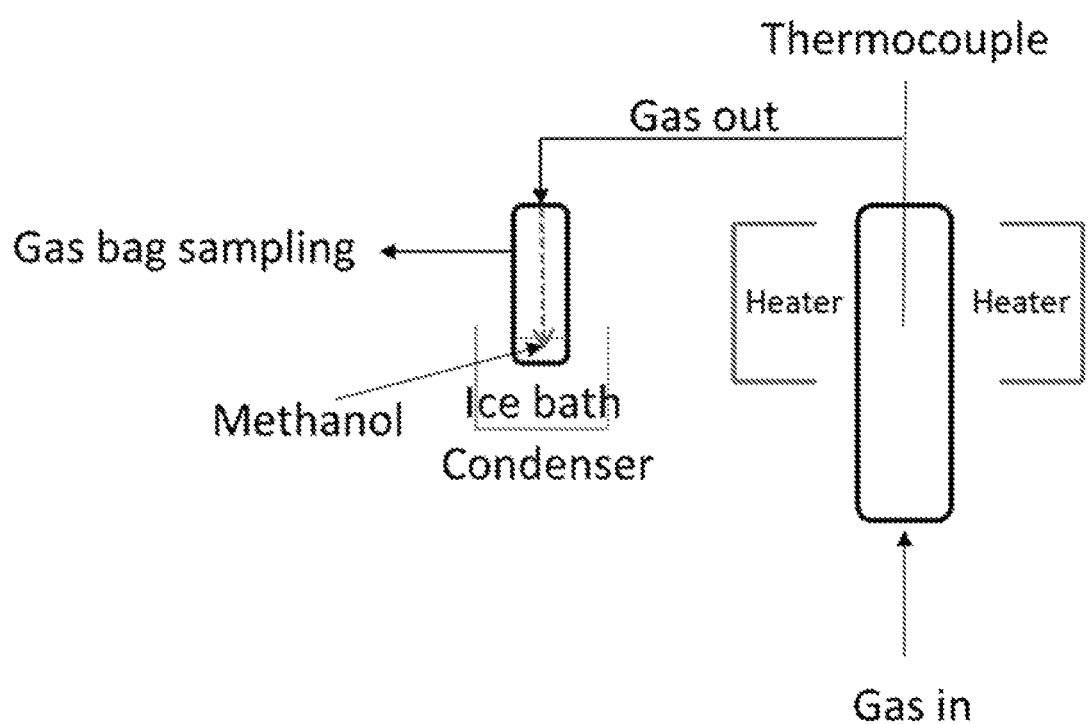
FIG. 6 is a simplified schematic block diagram of a reactor and process in accordance with aspects of the invention.

A reactor schematically shown in FIG. 6 was charged with 5 g of gamma alumina, average particle size of 44 micron. The charge was fluidized with a 200 ml/min upward flow of nitrogen. The reactor was brought to 600° C. with an external electrical heater. A 0.5 g charge of high-density polyethylene (HDPE) was introduced from the top of the reactor and brought in contact with the bubbling bed of alumina. The gas and liquid products resulting were analyzed by GC. Results are in FIG. 4, labeled pyrolysis. The plastic was >95% converted in 5 minutes. The product contained 17 mole % hydrogen and 6 mole % ethylene.

Example 2. (Invention)

A catalyst, i.e., a metal oxide oxygen transfer agent, was prepared that contained 0.5% $MnO_2$, 11% CuO, 18% CaO and the balance gamma alumina by weight. The gamma alumina functions as the support for the metal oxide. The metal oxide oxygen transfer agent was charged to the reactor and run with HDPE, under the same conditions as in Example 1. The plastic was >95% converted at 600° C. in 4 minutes. The product, shown in FIG. 4, as Cu OTA, contained 9% hydrogen and 15% ethylene. Compared to Example 1, this catalyst produced less hydrogen because the in-situ produced hydrogen was converted to water by the metal oxide. The color of the metal oxide catalyst changed from dark grey to pink, indicating its reduction. The ethylene yield was higher than in Example 1, indicating the beneficial effect of the catalytic metal oxide oxygen transfer agent (OTA).

Example 3. (Invention)

A catalyst, i.e., a metal oxide oxygen transfer agent, was prepared that contained 0.5% $MnO_2$, 11% CuO, 18% CaO and the balance gamma alumina support by weight. This catalyst was mixed with ZSM-5 zeolite with a silica to alumina ratio of 23. The mixture of metal oxide oxygen transfer agent (catalyst) to zeolite was 1 to 1 by weight. The mixed catalyst was charged to the reactor and run with HDPE, under the same reactor conditions as in Example 1. The plastic was >95% converted at 600° C. in 4 minutes. The product, shown as Cu OTA+ZSM5 SAR 23 in FIG. 4, contained 1.5% hydrogen and 17% ethylene. Compared to Examples 1 and 2, this physical mixture of the metal oxide oxygen transfer agent and the ZSM-5 zeolite produced less hydrogen because the in-situ produced hydrogen was converted to water by the metal oxide catalyst. The color of the metal oxide catalyst changed from dark grey to pink, indicating its reduction. The ethylene yield was higher than in Example 1, indicating the beneficial effect of the catalytic metal oxide OTA and zeolite co-catalyst.

Example 4. (Invention)

A catalyst, i.e., a metal oxide oxygen transfer agent, was prepared that contained 0.5% $MnO_2$, 11% CuO, 18% CaO and the balance gamma alumina support by weight. This metal oxide oxygen transfer agent was mixed with ZSM-5 with a silica to alumina ratio of 30. The mixture of metal oxide oxygen transfer agent to zeolite was 1 to 1 by weight. The mixture of catalysts, i.e. the metal oxide oxygen transfer agent and the ZSM-5 was charged to the reactor and run with HDPE, using the same conditions as in Example 1. The plastic was >95% converted at 600° C. in 4 minutes. The product, shown as Cu OTA+ZSM5 SAR 30 in FIG. 4, contained 6% hydrogen and 14% ethylene. Compared to Example 1, this mixture of catalysts produced less hydrogen because the in-situ produced hydrogen was converted to water by the metal oxide oxygen transfer agent. The color of the metal oxide oxygen transfer agent catalyst changed from dark grey to pink, indicating its reduction. The ethylene yield was higher than in Example 1 indicating the beneficial effect of the catalytic oxygen transfer agent and zeolite co-catalyst.

Example 5. (Invention)

A catalyst, i.e., a metal oxide oxygen transfer agent, was prepared that contained 0.5% $MnO_2$, 11% CuO, 18% CaO and the balance gamma alumina support by weight. This metal oxide oxygen transfer agent catalyst was mixed with zeolite Y with a silica to alumina ratio of 5.2. The mixture of metal oxide oxygen transfer agent to zeolite Y was 1 to 1 by weight. The mixed catalyst was charged to the reactor and run with HDPE, as in Example 1. The plastic was >95% converted at 600 C in 4 minutes. The product, shown as Cu OTA+Y SAR 2 in FIG. 4, contained 3% hydrogen and 7% ethylene. Compared to Example 1, this catalyst mixture of the produced less hydrogen because the in-situ produced hydrogen was converted to water by the metal oxide. The ethylene yield was higher than in Example 1 indicating the beneficial effect of the catalytic oxygen transfer agent and zeolite co-catalyst.

Example 6. (Invention)

A catalyst, i.e., a metal oxide oxygen transfer agent, was prepared that contained 0.5% $MnO_2$, 11% CuO, 18% CaO and the balance gamma alumina by weight. This catalyst was mixed with an fluid catalytic cracking (FCC) [Ecat® (W.R. Grace)] catalyst. The mixture of metal oxide oxygen transfer agent to FCC was 1 to 1 by weight. The mixed catalyst was charged to the reactor and run with HDPE, as in Example 1. The plastic was >95% converted at 600° C. in 4 minutes. The product, shown as Cu OTA+FCC in FIG. 4, contained <1% hydrogen and 4% ethylene. Compared to Example 1, this catalyst produced less hydrogen because the in-situ produced hydrogen was converted to water by the metal oxide.

Example 7. (Invention)

A catalyst was prepared by making an intimate physical mixture of ammonium exchanged form of zeolite Y with 3.26 g cupric chloride in an amount that yielded a 1:1 copper to aluminum ratio. The catalyst was dried at 110° C. and then calcined in air at 600° C. for 16 hours. The resulting material was stirred in an aqueous solution of 10% tri-n-butyl ammonium chloride for two hours. After filtration of the solid catalyst, the material was again calcined at 600° C. for 16 hours. The catalyst was used for the conversion of HDPE following the procedures of Example 1. The plastic was >95% converted to products at 600° C. in 3 minutes.

Compared to Example 1, the product gas has an ethylene to ethane ratio of 8.75% compared to a ratio of 3.25%, therefore demonstrating the beneficial effect of the method for increasing the production of ethylene.

These examples indicate the beneficial effect of using catalytic metal oxide oxygen transfer agents with zeolite co-catalyst for the in-situ conversion of hydrogen to water by the metal oxide oxygen transfer agent and increasing the yield of ethylene from HDPE conversion. The in-situ hydrogen conversion generates heat, which may be used to drive the otherwise endothermic pyrolytic conversion of plastics to olefins. Within this specification embodiments have been described in a way which enables a clear and concise specification to be written, but it is intended and will be appreciated that embodiments may be variously combined or separated without departing from the invention. For example, it will be appreciated that all preferred features described herein are applicable to all aspects of the invention described herein.

The foregoing description of various forms of the invention has been presented for purposes of illustration and description. It is not intended to be exhaustive or to limit the invention to the precise forms disclosed. Numerous modifications or variations are possible in light of the above teachings. The forms discussed were chosen and described to provide the best illustration of the principles of the invention and its practical application to thereby enable one of ordinary skill in the art to utilize the invention in various forms and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method of producing one or more olefins by oxidative dehydrogenation of a hydrocarbon feed having a feed weight average molecular weight, the method comprising:
    a) contacting, in a first vessel, the hydrocarbon feed with:
        i) at least one oxidized oxygen transfer agent comprising at least one metal oxide; and
    b) oxidatively dehydrogenating the hydrocarbon feed at reaction conditions to produce a product stream comprising the one or more olefins and hydrogen;
wherein at least a portion of the at least one oxidized oxygen transfer agent is reduced by the hydrogen at the reaction conditions to produce at least one reduced oxygen transfer agent and water; and
    c) combining at least a portion of the at least one reduced oxygen transfer agent with a source of oxygen to produce at least a first portion of the oxidized oxygen transfer agent and heat, wherein the first portion of oxidized oxygen transfer agent and/or the heat are fed to step a);
wherein the i) at least one oxidized oxygen transfer agent is in combination with at least one zeolite;
wherein inner channels of the at least one zeolite are from 3 to 8 Angstroms, the at least one zeolite has an acid nature, and the acid nature of the at least one zeolite is only on the exterior surfaces thereof;
wherein the at least one zeolite is selected from the group consisting of zeolite Y, ZSM-5, and mixtures thereof;
wherein the at least one metal oxide comprises oxides of Mn, oxides of Cu, and oxides of Ca; and
wherein the hydrocarbon feed comprises at least one polymer having a weight average molecular weight of 1000 Daltons or higher.

2. The method according to claim 1, wherein the product stream further comprises at least one hydrocarbon having a lower weight average molecular weight than the hydrocarbon feed weight average molecular weight and the at least one hydrocarbon having a lower weight average molecular weight than the hydrocarbon feed weight average molecular weight is fed to step a).

3. The method according to claim 2, wherein the one or more olefins comprise at least one of ethylene and propylene.

4. The method according to claim 1, wherein the process further comprises the step of:
    d) feeding, to a second vessel:
        ii) at least a portion of the hydrogen produced in step b); and
        iii) a gas comprising oxygen;
    wherein the portion of the hydrogen and the oxygen are combusted to produce heat that is fed to step a).

5. The method according to claim 4, wherein the product stream further comprises at least one hydrocarbon having a lower weight average molecular weight than the hydrocarbon feed weight average molecular weight and step d) further comprises feeding, to the second vessel, at least a portion of the at least one hydrocarbon having a lower weight average molecular weight than the hydrocarbon feed weight average molecular weight and combusting the portion of the at least one hydrocarbon having a lower weight average molecular weight than the hydrocarbon feed weight average molecular weight with the oxygen to produce heat that is fed to step a).

6. The method according to claim 1, wherein step c) further comprises:
    feeding, to a regeneration vessel:
        iv) the portion of the reduced oxygen transfer agent; and
        v) a gas comprising oxygen;
    wherein the portion of the reduced oxygen transfer agent is oxidized to form at least a second portion of the oxidized oxygen transfer agent and the second portion of the oxidized oxygen transfer agent is fed to step a).

7. The method according to claim 1, wherein the at least one oxidized oxygen transfer agent includes at least one oxide of sulfur selected from the group consisting of sulfur dioxide; sulfur trioxide; $CaSO_4$; sulfate salts of Mn, Fe, Sm, Ga, Ti, W, Mo, V, Nb, Cr, K, Cs, Rb, P, Cu, Pb, Ni, and As; and mixtures thereof.

8. The method according to claim 1, wherein the at least one oxidized oxygen transfer agent comprises $MnO_2$, CuO, and CaO.

9. The method according to claim 1, wherein step a) further comprises contacting the hydrocarbon feed with at least one solid acid catalyst selected from the group consisting of zeolite Y, zeolite A, faujasite, bentonite, sodalite, ZSM-10, MCM-68, MCM-61, MCM-35, ZSM-39, ZSM-23, ZSM-12, SAPO 56, AlPO-5, AlPO-14, AlPO-41, and mixtures thereof.

10. The method according to claim 1, wherein step a) further comprises contacting the hydrocarbon feed with at least one fluidic cracking catalyst.

11. The method according to claim 1 wherein the at least one polymer is selected from the group consisting of low density polyethylene, linear low density polyethylene, high density polyethylene, polystyrene, polyethylene terephthalate, poly vinyl chloride, polypropylene, polyurethanes, and mixtures thereof.

12. The method according to claim 1, wherein the hydrocarbon feed comprises plastic waste.

13. The method according to claim 1, wherein the hydrocarbon feed comprises a mixture of hydrocarbons having an average of at least 7 carbon atoms per molecule.

14. The method according to claim 1, wherein the reaction conditions comprise a temperature between 350° C. and 1000° C. and a pressure from 0.9 to 10 atm.

15. The method according to claim 1, wherein the metal oxide comprises from 60% to 90% by weight of the total weight of the zeolite and the metal oxide.

16. The method according to claim 1, wherein the at least one metal oxide further comprises a metal oxide selected from the group consisting of oxides of La, oxides of Pr, oxides of Tb, oxides of Nd, oxides of Dy, and mixtures thereof.

17. The method according to claim 15, wherein the at least one metal oxide further comprises a metal oxide selected from the group consisting of oxides of La, oxides of Pr, oxides of Tb, oxides of Nd, oxides of Dy, and mixtures thereof.

18. A method of producing one or more olefins by oxidative dehydrogenation of a hydrocarbon feed comprising at least one polymer having a weight average molecular weight of 1000 Daltons or higher, the method comprising:

a) contacting, in a first vessel, the hydrocarbon feed with:
  i) at least one oxidized oxygen transfer agent comprising at least one metal oxide; and
  b) oxidatively dehydrogenating the hydrocarbon feed at reaction conditions to produce a product stream comprising the one or more olefins and hydrogen;

wherein at least a portion of the at least one oxidized oxygen transfer agent is reduced by the hydrogen at the reaction conditions to produce at least one reduced oxygen transfer agent and water; and c) feeding, to a regeneration vessel, at least a portion of the at least one reduced oxygen transfer agent with a source of oxygen to produce at least a first portion of the oxidized oxygen transfer agent and heat, wherein the first portion of oxidized oxygen transfer agent and the heat are fed to the first vessel in step a) from the regeneration vessel;

wherein the i) at least one oxidized oxygen transfer agent is in combination with at least one zeolite; and wherein inner channels of the at least one zeolite are from 3 to 8 Angstroms, the at least one zeolite has an acid nature, and the acid nature of the at least one zeolite is only on the exterior surfaces thereof.

* * * * *